(12) United States Patent
Sarry et al.

(10) Patent No.: US 11,376,269 B2
(45) Date of Patent: Jul. 5, 2022

(54) PHARMACEUTICAL COMPOSITIONS FOR THE TREATMENT OF CHEMORESISTANT ACUTE MYELOID LEUKEMIA (AML)

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); CENTRE HOSPITALIER UNIVERSITAIRE DE TOULOUSE, Toulouse (FR)

(72) Inventors: Jean-Emmanuel Sarry, Toulouse (FR); Christian Recher, Toulouse (FR); Fabienne De Toni-Costes, Toulouse (FR); Nesrine Aroua, Toulouse (FR)

(73) Assignees: INSERM, Paris (FR); UNIVERSITE PAUL SABATIER TOULOUSE III, Toulouse (FR); CENTRE HOSPITALIER UNIVERSITAIRE DE TOULOUSE, Toulouse (FR)

(*) Notice: Subject to any disclaimer, the term of this patent is extended or adjusted under 35 U.S.C. 154(b) by 1 day.

(21) Appl. No.: 16/099,209

(22) PCT Filed: May 5, 2017

(86) PCT No.: PCT/EP2017/060756
§ 371 (c)(1),
(2) Date: Nov. 6, 2018

(87) PCT Pub. No.: WO2017/191300
PCT Pub. Date: Nov. 9, 2017

(65) Prior Publication Data
US 2019/0209594 A1 Jul. 11, 2019

(30) Foreign Application Priority Data
May 6, 2016 (EP) .................................... 16305531

(51) Int. Cl.
| | |
|---|---|
| A61K 31/704 | (2006.01) |
| A61K 31/663 | (2006.01) |
| A61K 31/7068 | (2006.01) |
| A61K 45/06 | (2006.01) |
| A61P 35/02 | (2006.01) |
| A61K 31/00 | (2006.01) |
| A61K 33/243 | (2019.01) |
| A61K 47/68 | (2017.01) |

(52) U.S. Cl.
CPC ............ *A61K 31/704* (2013.01); *A61K 31/00* (2013.01); *A61K 31/663* (2013.01); *A61K 31/7068* (2013.01); *A61K 33/243* (2019.01); *A61K 45/06* (2013.01); *A61K 47/6873* (2017.08); *A61P 35/02* (2018.01)

(58) Field of Classification Search
CPC .. A61K 31/704; A61K 47/6873; A61K 31/00; A61K 31/663; A61K 31/7068; A61K 33/24; A61K 45/06; A61P 35/02
USPC ....................................................... 424/181.1
See application file for complete search history.

(56) References Cited

U.S. PATENT DOCUMENTS 6,121,320 A    9/2000 Doukas

FOREIGN PATENT DOCUMENTS

WO    2012/085132 A1    6/2012

OTHER PUBLICATIONS

Gura (Science. 1997; 278: 1041-1042).*
Dennis (Nature. Aug. 7, 2006; 442: 739-741).*
Abe et al., "Increased Expression of Insulin-Like Growth Factor I is Associated with Ara-C Resistance in Leukemia", Tohoku J. Exp. Med, Jan. 1, 2006, pp. 217-228.
Man et al., "A novel tescalcin-sodium/hydrogen exchange axis underlying sorafenib resistance in FLT3-ITD+ AML", Blood, vol. 123, No. 16, Mar. 7, 2014, pp. 2530-2539.
Marteau et al., "Pharmacological Characterization of the Human P2Y13 Receptor", Molecular Pharmacology, American Society for Pharmacology and Experimental Therapeutics, US, vol. 64, No. 1, Jan. 1, 2003, pp. 104-112.
Michaud et al., "Subversion of the chemotherapy-induced anticancer immune response by the ecto-ATPase CD39", Oncoimmunology, vol. 1, No. 3, May 1, 2012, pp. 393-395.
Dulphy et al., "Contribution of CD39 to the immunosuppressive microenvironment of acute myeloid leukaemia at diagnosis", Br. J. Haematology, Jan. 1, 2014, pp. 722-740.

* cited by examiner

*Primary Examiner* — Yan Xiao
(74) *Attorney, Agent, or Firm* — WC&F IP

(57) ABSTRACT

The present invention relates to pharmaceutical compositions for use in the treatment of chemoresistant acute myeloid leukemia (AML). The inventors have established a powerful preclinical model to screen in vivo responses to conventional genotoxics and to mimic the chemoresistance and minimal residual disease as observed in AML patients after chemotherapy. The inventors showed that cytarabine-resistance mechanism involves the CD39-dependent crosstalk between energetic niche and AML mitochondrial functions through CD39-P2Y13-cAMP-PKA signaling axis. In particular, the present invention relates to an inhibitor of the CD39-P2Y13-cAMP-PKA signaling axis for use in a method of treating chemoresistant acute myeloid leukemia (AML) in a patient in need thereof comprising administering to the patient a therapeutically effective amount of said inhibitor.

2 Claims, 14 Drawing Sheets

Figure 1A:
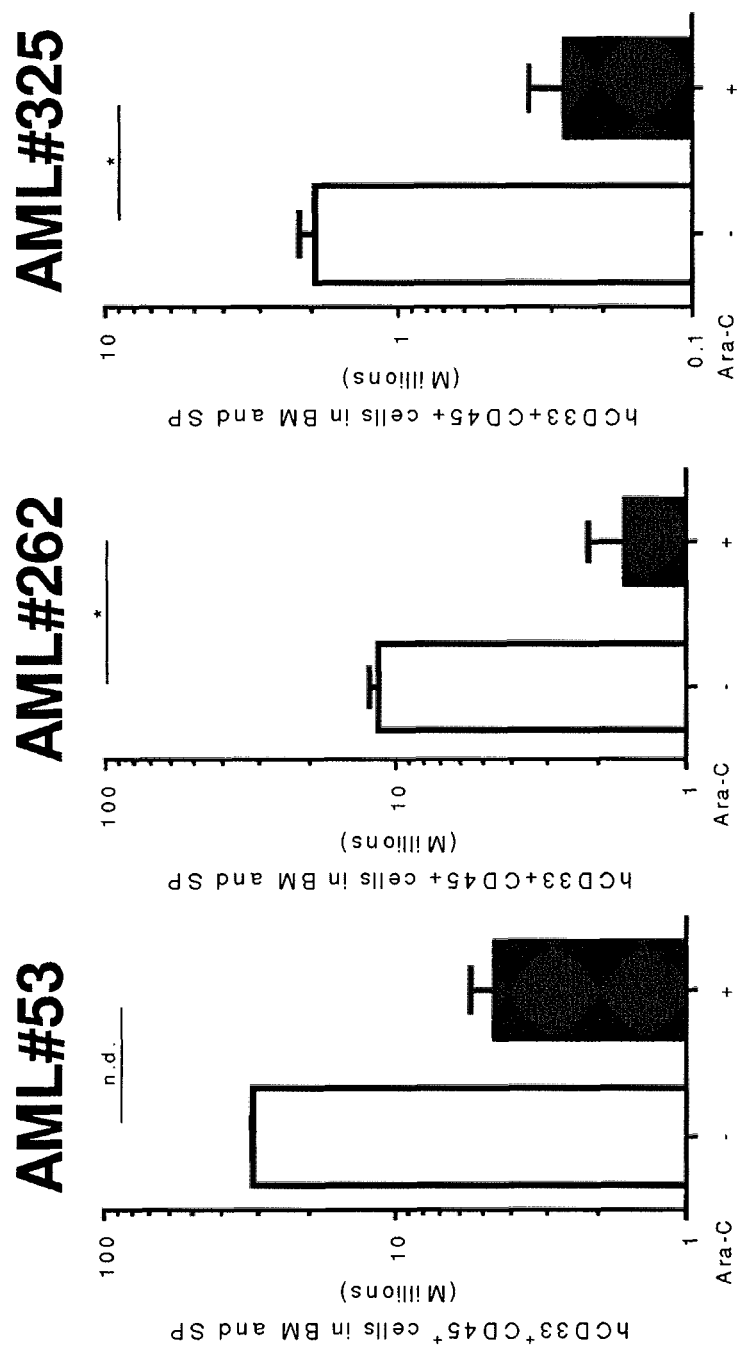
Figure 1A:
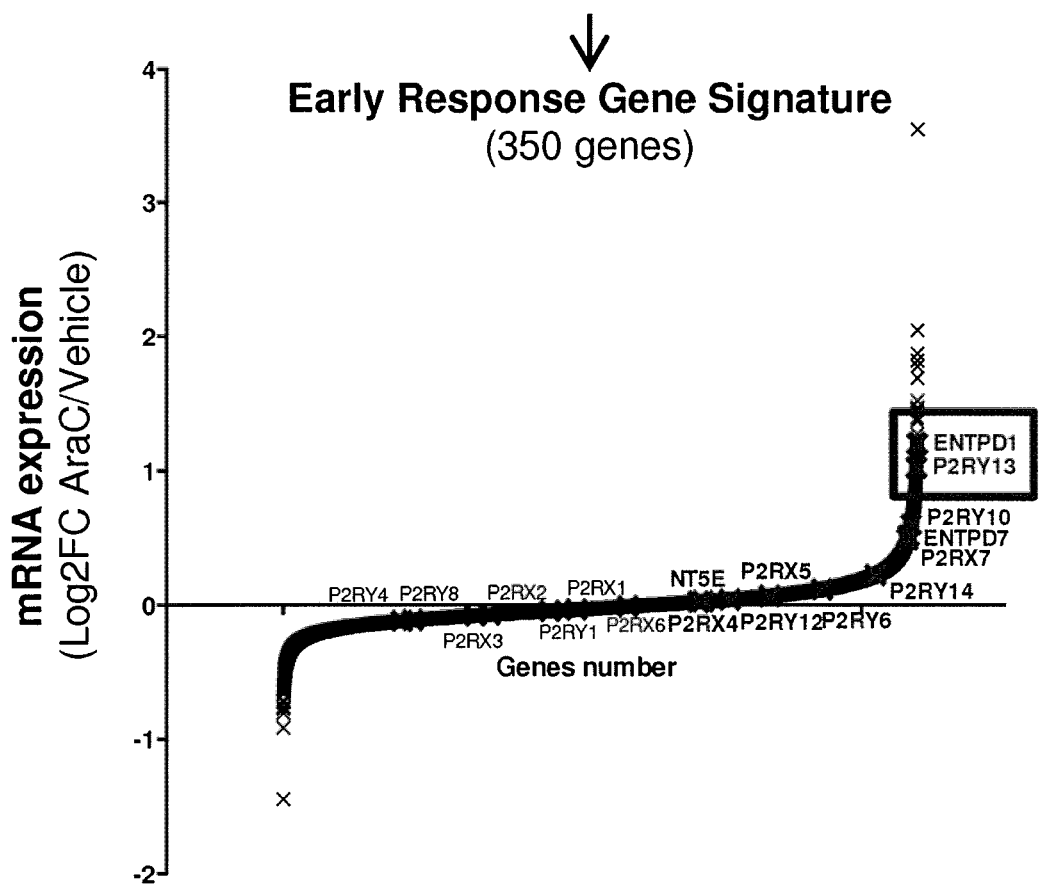

PHARMACEUTICAL COMPOSITIONS FOR THE TREATMENT OF CHEMORESISTANT ACUTE MYELOID LEUKEMIA (AML)

FIELD OF THE INVENTION

The present invention relates to methods and pharmaceutical compositions for the treatment of chemoresistant acute myeloid leukemia (AML).

BACKGROUND OF THE INVENTION

Chemotherapy resistance is the major therapeutic barrier in acute myeloid leukemia (AML). AML is the most common adult leukemia. It is characterized by clonal expansion of immature myeloblasts and initiates from rare leukemic stem cells (LSCs). Despite a high rate of complete remission after conventional front-line induction chemotherapy (e.g. daunorubicin, DNR, or idarubicin, IDA plus cytarabine, AraC), the prognosis is very poor in AML. To date, 5-year overall survival is still about 30 to 40% in patients younger than 60 years old and less than 20% in patients over 60 years. This results from the high frequency of distant relapses (50 and 85% before and after the age of 60, respectively) caused by tumor regrowth initiated by chemoresistant leukemic clones (RLCs) and characterized by a refractory phase during which no other treatment has shown any efficacy thus far (Tallman et al. 2005; Burnett et al. 2011). AML is one of the rare hematological malignancies, for which therapy has not significantly improved during the past 30 years despite intense research efforts. Therefore, understanding the causes of chemoresistance is crucial for the development of new treatments eradicating RLCs to overcome AML patient relapses.

The biology of therapeutic resistance (drug efflux, detoxification enzymes, inaccessibility of the drug to the leukemic niche) currently represents an active area of research. However, the molecular mechanisms underlying AML chemoresistance are still poorly understood, especially in vivo. It is nevertheless increasingly recognized that the causes of chemoresistance and relapse reside within a small cell population. Supporting this idea, a recent clinical study has shown that the presence of high levels of CD34$^+$CD38$^{low/-}$CD123$^+$cells at diagnosis correlates with adverse outcome in AML patients in terms of response to therapy and overall survival (Vergez et al, 2011 Haematologica). Consistent with these data, Ishikawa and colleagues (2007) have observed that this population is also the most resistant to AraC in vivo. As a first step towards successful therapeutic eradication of these RLCs, it is now necessary to comprehensively profile their dominant intrinsic and acquired characteristics.

CD39/ENTPD1 (ectonucleoside triphosphate diphosphohydrolase-1) is a protein of the membrane surface, actor of the adenosine signaling pathway. In fact, CD39 decreases extracellular ATP (immunogenic inducer) and generates immunosuppressive adenosine, which potently inhibits host immune responses against cancer. CD39 also has a role in the immunosurveillance and inflammatory response. Furthermore, although other NTPDases exist, CD39 appears to be the main NTPDase in T lymphocytes and regulatory T cells (CD4+CD25+Foxp3+) (Bastid et al, 2013 Oncogene). Recent lines of evidence have revealed high expression and activity of CD39 in several blood or solid tumors (head and neck cancer, thyroid cancer, colon cancer, pancreatic cancer, kidney cancer, testis cancer, and ovarian cancer), implicating potential roles for this enzyme in promoting tumor growth and infiltration (Bastid et al. Cancer Immunol Res. 2015 March; 3(3):254-65.). Also, CD39 is frequently detected in primary tumor cells, cancer exosomes, tumor associated endothelial cells and AML blasts. CD39 contributes to the immunosuppressive microenvironment in AML (Dulphy et al. Br J Haematol. 2014 June; 165(5):722-5). In fact, extracellular nucleotides (ATP, UTP) can inhibit AML homing and engraftment in NSG mice (Salvestrini et al. Blood. 2012 Jan. 5; 119(1):217-26).

SUMMARY OF THE INVENTION

The present invention relates to methods and pharmaceutical compositions for the treatment of chemoresistant acute myeloid leukemia (AML). In particular, the present invention is defined by the claims.

DETAILED DESCRIPTION OF THE INVENTION

The inventors have established a powerful preclinical model to screen in vivo responses to conventional genotoxics and to mimic the chemoresistance and minimal residual disease as observed in AML patients after chemotherapy (Farge T, Sarry J E et al, Chemotherapy resistant human acute myeloid leukemia cells are not enriched for leukemic stem cells but require oxidative metabolism. CANCER DISCOVERY. 2017). Based on this model and the current hypothesis that AraC-resistant cells are rare, replicatively dormant and well adapted to hypoxic conditions, the inventors have further analyzed all of these characteristics in AraC-treated patient-xenografted mice. They have first confirmed that CD34+CD38− cell population is increased post-AraC chemotherapy in residual AML cells. Surprisingly, the inventors have found that AraC treatment equally kills both cycling and quiescent cells as well as LSCs in vivo. Strikingly, cytarabine-resistant pre-existing and persisting cells displayed high levels of reactive oxygen species, showed increased mitochondrial mass, and retained active polarized mitochondria, consistent with a high oxidative phosphorylation (OXPHOS) status (Farge T, Sarry J E et al, Chemotherapy resistant human acute myeloid leukemia cells are not enriched for leukemic stem cells but require oxidative metabolism. CANCER DISCOVERY. 2017). Moreover, they observed that AraC chemotherapy induced an apoptotic cell death in vivo and they have identified a signature of 15 genes (amongst of 350 genes, including CD39), that are the most differentially expressed in all of the three AML patient xenografts after AraC treatment as compared to control samples using their in vivo PDX models coupled to a gene expression analysis. Finally, the inventors showed that cytarabine-resistance mechanism involves the CD39-dependent crosstalk between energetic niche and AML mitochondrial functions through CD39-P2Y13-cAMP-PKA signalling axis.

Accordingly, one object of the present invention relates to a method of treating chemoresistant acute myeloid leukemia (AML) in a patient in need thereof comprising administering to the patient a therapeutically effective amount of an inhibitor of the CD39-P2Y13-cAMP-PKA signalling axis.

As used herein, the term "acute myeloid leukemia" or "acute myelogenous leukemia" ("AML") refers to a cancer of the myeloid line of blood cells, characterized by the rapid growth of abnormal white blood cells that accumulate in the bone marrow and interfere with the production of normal blood cells.

As used herein; the term "chemoresistant acute myeloid leukemia" refers to the clinical situation in a patient suffering from acute myeloid leukemia when the proliferation of cancer cells cannot be prevented or inhibited by means of a chemotherapeutic agent or a combination of chemotherapeutic agents usually used to treat AML, at an acceptable dose to the patient. The leukemia can be intrinsically resistant prior to chemotherapy, or resistance may be acquired during treatment of leukemia that is initially sensitive to chemotherapy.

As used herein, the term "chemotherapeutic agent" refers to any chemical agent with therapeutic usefulness in the treatment of cancer. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these drugs are directly toxic to cancer cells and do not require immune stimulation. Suitable chemotherapeutic agents are described, for example, in Slapak and Kufe, Principles of Cancer Therapy, Chapter 86 in Harrison's Principles of Internal medicine, 14th edition; Perry et at, Chemotherapeutic, Ch 17 in Abeloff, Clinical Oncology 2nd ed., 2000 ChrchillLivingstone, Inc.; Baltzer L. and Berkery R. (eds): Oncology Pocket Guide to Chemotherapeutic, 2nd ed. St. Louis, mosby-Year Book, 1995; Fischer D. S., Knobf M. F., Durivage H J. (eds): The Cancer Chemotherapeutic Handbook, 4th ed. St. Louis, Mosby-Year Handbook. In some embodiments the chemotherapeutic agent is cytarabine (cytosine arabinoside, Ara-C, Cytosar-U), quizartinib (AC220), sorafenib (BAY 43-9006), lestaurtinib (CEP-701), midostaurin (PKC412), carboplatin, carmustine, chlorambucil, dacarbazine, ifosfamide, lomustine, mechlorethamine, procarbazine, pentostatin, (2'deoxycoformycin), etoposide, teniposide, topotecan, vinblastine, vincristine, paclitaxel, dexamethasone, methylprednisolone, prednisone, all-trans retinoic acid, arsenic trioxide, interferon-alpha, rituximab (Rituxan®), gemtuzumab ozogamicin, imatinib mesylate, Cytosar-U), melphalan, busulfan (Myleran®), thiotepa, bleomycin, platinum (cisplatin), cyclophosphamide, Cytoxan®)., daunorubicin, doxorubicin, idarubicin, mitoxantrone, 5-azacytidine, cladribine, fludarabine, hydroxyurea, 6-mercaptopurine, methotrexate, 6-thioguanine, or any combination thereof. In some embodiments, the leukemia is resistant to a combination of daunorubicin, or idarubicin plus cytarabine (AraC).

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

The method of the present invention is particularly suitable for preventing relapse of a patient suffering from AML who was treated with chemotherapy (e.g. AraC). As used herein, the term "relapse" refers to the return of cancer after a period of improvement in which no cancer could be detected. Thus, the method of the present invention is particularly useful to prevent relapse after putatively successful treatment with chemotherapy (e.g. AraC).

In some embodiments, the inhibitor of the CD39-P2Y13-cAMP-PKA signaling axis is a CD39 inhibitor.

As used herein, the term "CD39" has its general meaning in the art and refers to the CD39 protein also named as ectonucleoside triphosphate diphosphohydrolase-1 (EN-TPD1). CD39 is an ectoenzyme that hydrolases ATP/UTP and ADP/UDP to the respective nucleosides such as AMP. Accordingly, the term "CD39 inhibitor" refers to a compound that inhibits the activity or expression of CD39.

In some embodiments, the inhibitor of the CD39-P2Y13-cAMP-PKA signaling axis is a P2Y13 inhibitor.

As used herein, the term "P2Y13" has its general meaning in the art and refers to the P2Y purinoceptor 13. P2Y13 belongs to the family of G-protein coupled receptors. This family has several receptor subtypes with different pharmacological selectivity, which overlaps in some cases, for various adenosine and uridine nucleotides. To date, 8 P2Y receptors have been cloned in humans: P2Y1, P2Y2, P2Y4, P2Y6, P2Y11, P2Y12, P2Y13 and P2Y14. P2Y13 is activated by ADP. An exemplary human nucleic acid sequence is accessible in GenBanl under the accession numbers NM_023914 or NM_028808. An exemplary human amino acid sequence is accessible in GenBanl under the accession numbers NP_795713 or NP_083084.

In some embodiments, the CD39 inhibitor is an antibody having specificity for CD39.

In some embodiments, the P2Y13 inhibitor is an antibody having specificity for P2Y13.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

As used herein, the term "specificity" refers to the ability of an antibody to detectably bind an epitope presented on an antigen, such as CD39 or P2Y13, while having relatively little detectable reactivity with non-CD39 or P2Y13 proteins or structures (such as other proteins presented on leukemic cells). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a CD39 or P2Y13 polypeptide). The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH:VL heterodimer which is usually expressed from a gene fusion including VH and VL encoding genes linked by a peptide-encoding linker. "dsFv" is a VH:VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH–VL). By using a linker that is too short to allow pairing between the two domains on the same chain, the domains are forced to pair with the complementary domains of another chain and create two antigen-binding sites.

Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e. CD39 or cell that express CD39). Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods. Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation. Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

The antibody of the present invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a human monoclonal antibody of the present invention may be switched by known methods. Typical, class switching techniques may be used to convert one IgG subclass to another, for instance from IgG1 to IgG2. Thus, the effector function of the human monoclonal antibodies of the present invention may be changed by isotype switching to, e.g., an IgG1, IgG2, IgG3, IgG4, IgD, IgA, IgE, or IgM antibody for various therapeutic uses. In some embodiments, the antibody of the present invention is a full-length antibody. In some embodiments, the full-length antibody is an IgG1 antibody. In some embodiments, the full-length antibody is an IgG4 antibody. In some embodiments, the OX1R-specific IgG4 antibody is a stabilized IgG4 antibody.

Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antbodies are disclosed in WO2008145142, which is hereby incorporated by reference in its entirety. In some embodiments, the human monoclonal antibody of the present invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

Monoclonal antibodies that are CD39 inhibitors are well known in the art and includes those described in the international patent application WO 2009095478, WO2012085132 and in the following publications: Bonnefoy N, Bastid J, Alberici G, Bensussan A, Eliaou J F. CD39: A complementary target to immune checkpoints to counteract tumor-mediated immunosuppression. Oncoimmunology. 2015 Feb. 3; 4(5):e1003015. eCollection 2015 May; Bastid J, Regairaz A, Bonnefoy N, Déjou C, Giustiniani J, Laheurte C, Cochaud S, Laprevotte E, Funck-Brentano E, Hemon P, Gros L, Bec N, Larroque C, Alberici G, Bensussan A, Eliaou J F. Inhibition of CD39 enzymatic function at the surface of tumor cells alleviates their immunosuppressive activity. Cancer Immunol Res. 2015 March; 3(3):254-65.

In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure : FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3.

In some embodiments, the CD39 inhibitor is an inhibitor of CD39 expression. In some embodiments, the P2Y13 inhibitor is an inhibitor of P2Y13 expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of CD39 or P2Y13 mRNA by binding thereto and thus preventing protein translation or increasing mRNA degradation, thus decreasing the level of CD39, and thus activity, in a cell. For example, antisense oligonucleotides of at least about 15 bases and complementary to unique regions of the mRNA transcript sequence encoding CD39 or P2Y13 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. CD39 or P2Y13 gene expression can be reduced by contacting a subject or cell with a small double stranded RNA (dsRNA), or a vector or construct causing the production of a small double stranded RNA, such that CD39 or P2Y13 gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing CD39 or P2Y13. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

In some embodiments, the P2Y13 inhibitor is selected from the group consisting of derivatives of PPADS (pyridoxal-5'-phosphate-6-azo-phenyl-2,4-disulfonate), described in Kim et al. (2005) Biochem. Pharmacol. 70:266-74, such as analogues of PPADS modified through substitution of the phenylazo ring, including halo and nitro substitution, and 5'-alkyl phosphonate analogues. Preferred are 6-(3-nitrophenylazo) derivatives of pyridoxal-5'-phosphate, the 2-chloro-5-nitro analogue (MRS 2211) and the 4-chloro-3-nitro analogue (MRS 2603). Other examples of compounds are NF023, TNP-ATP, suramin, PPADS, DIDS (4,4'-diisothiocyanatostilbene-2,2'-disulfonic acid), Ip5I and PPNDS. The compound AR-C67085 is a further example of a preferred compound (Wang (2005) Circ Res. 96(2):189-96). P2Y13 antagonists can be identified as described in U.S. Pat. No. 6,946,244.

In some embodiments, the inhibitor of the CD39-P2Y13-cAMP-PKA signaling axis is selected from the group consisting of suramin, periodate oxidized adenosine 5'-triphosphate ("Oxidized-ATP"), brilliant blue G ("BBG"), hexamethylene amiloride ("HMA"), diinosine pentaphosphate ("Ip5I"), pyridoxal-5'-phosphate-6-azophenyl-2',5'-disulphonic acid ("isoPPADS"), 1-[N,O-bis(5-isoquinolinesulfonyl)-N-methyl-L-tyrosyl]-4-phenyl-piperazine ("KN-62"), pyridoxal-5'-phosphate-6-azophenyl-4'-carboxylate ("MRS 2159"), 8,8'-(carbonylbis(imino-3,1-phenylenecarbonylimino)bis(1,3,5-napththalene-trisulfonic acid) ("NF023"), 8,8'-(carbonylbis(imino-4,1-phenylenecarbonylimino-4,1-phenylenecarbonylimino)bis(1,3,5-napththalenetrisulfonic acid) ("NF279"), pyridoxal-5'-phosphate-6-(2'-naphthylazo-6-nitro-4',8'-disulphonate) ("PPNDS"), reactive blue 2 ("RB-2"), 2',3'-O-(2,4,6-trinitrophenyl) adenosine triphosphate ("TNP-ATP"), adenosine 3'-phosphate 5'-phosphosulphate ("A3P5PS"), 2'-deoxy-N-6-methyladenosine-3',5'-bisphosphate ("MRS 2179"), (N)-methanocarba-N-6-methyl-2-chloro-2'-deoxy-adenosine-3',5'-bisphosphate ("MRS 2279"), pyridoxal-5'-phosphate-6-azophenyl-2',4'-disulphonic acid ("PPADS"), N6-[2-(methylthio)-ethyl]-2-(3,3,3-trifluoropropyl)thio-5'-adenylic acid ("AR-C69931MX"), N1-(6-ethoxy-1,3-benzothiazol-2-yl-2-(7-ethoxy-4-hydroxy-2,2-dioxo-2H-2-6benzo[4,5][1,3]thiazolo[2,3-c]-[1,2,4]thiadiazin-3-yl)-2-oxo-1-ethanesulfonamide ("C1330-7"), 2-methylthioadenosine-5'-monophosphate ("2-MeSAMP"), 8-cyclopentyl-1,3-dimethylxanthine ("CPT"), 8-cyclopentyl-1,3-dipropylxanthine ("CPX"), 3-(3-Iodo-4-aminobenzyl)-8-(4-oxyacetate)-phenyl-1-propyl xanthine ("I-ABOPX"), 1,3-diethyl-8-(3,4-dimethoxyphenylethyl)-7-methyl-3-,7-dihydro-1H-purine-2,6-dione ("KW 6002"), 3-ethyl 5-benzyl 2-methyl-6-phenyl-4-phenylethynyl-1,4-(.+-.)-dihydropyridine-3,5-dicarbox-ylate ("MRS 1191"), 2,3-diethyl-4,5-dipropyl-6-phenylpyridine-3-thiocarbo-xylate-5-carboxylate ("MRS 1523"), 9-chloro-2-(2-furyl)-5-phenylacetylamin-o[1,2,4]-triazolo[1,5-c]quinazoline ("MRS 1220"), N6-cyclopentyl-9-methyladenine ("N-0840"), N-(2-methoxyphenyl)-N'-(2-(3-pyridyl)quinazolin-4-yl)urea ("VUF 5574"), 8-(N-methylisopropyl)amino-N-(5'-endohydroxy-endonorbornyl)-9-methyladenine ("WRC-0571"), 8-[4-[[[[(2-aminoethyl)amino]carbonyl]methyl]oxy]phenyl]-1,3-dipropylxanthine, xanthine amine congener ("XAC"), 8-[4-[[(4-cyano)phenylcarbamoylmethyl]oxy]phenyl]-1,3-di-(n-propyl)xanthine ("MRS 1754"), 8-(3-chlorostyryl)caffeine, and alloxazine.

By a "therapeutically effective amount" of the inhibitor as above described is meant a sufficient amount to provide a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically, the inhibitor of the present invention is combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the inhibitor at the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The invention will be further illustrated by the following figures and examples. However, these examples and figures should not be interpreted in any way as limiting the scope of the present invention.

FIGURES

FIG. 1. Identification of new targets (eg. CD39/ENTPD1 and P2Y13) of the early cytarabine (AraC) resistance response in AML cells and analysis of their gene expression in human tissues, normal hematopoietic cells and AML patient cells. (A) Transcriptomic analysis of human residual AML cells purified from AraC-treated xenografted mice compared to PBS/control-treated xenografted mice (de Toni et al. in preparation). (B) ENTPD1 and P2Y13 gene expression in various human tissues (from Dezso. BMC Biol, 2008). (C) ENTPD1 and P2Y13 mRNA expression profiles in human normal myeloid system and human AML from HemaExplorer database. (D) Co-expression of ENTPD1 and P2Y13 gene in two independent transcriptomic studies of AML patients (MILE and METZLER).

Figure 2:
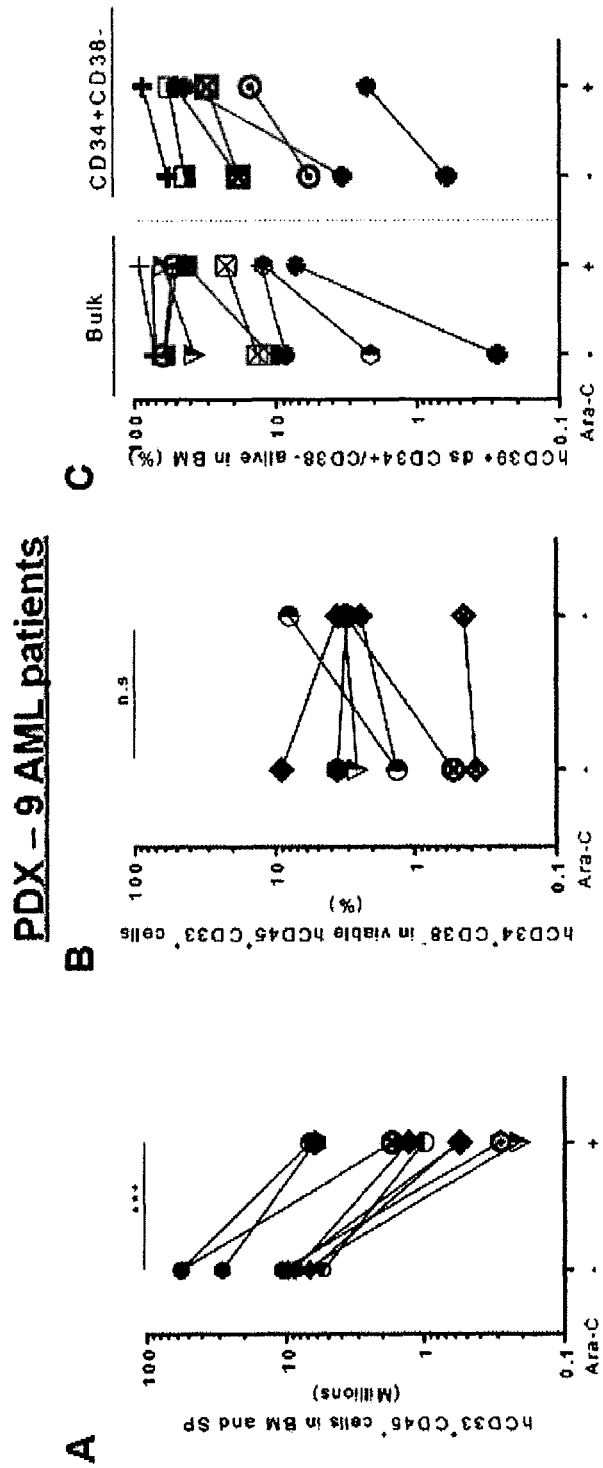
Figure 2:
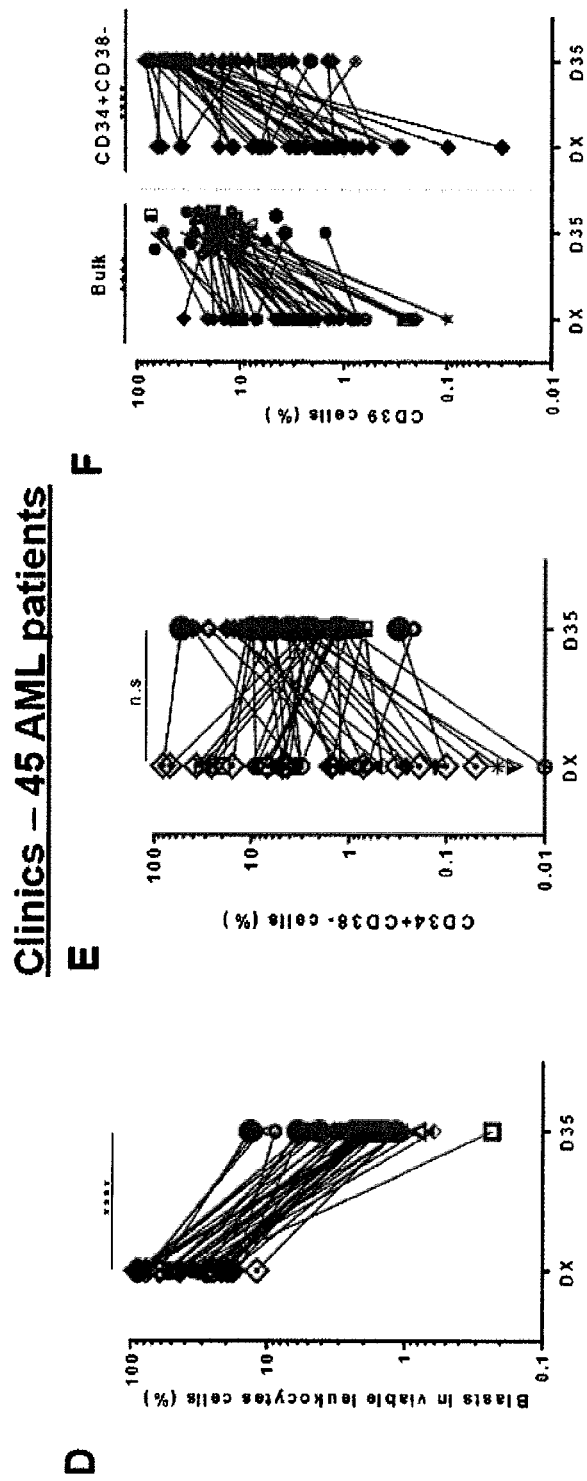
Figure 2:
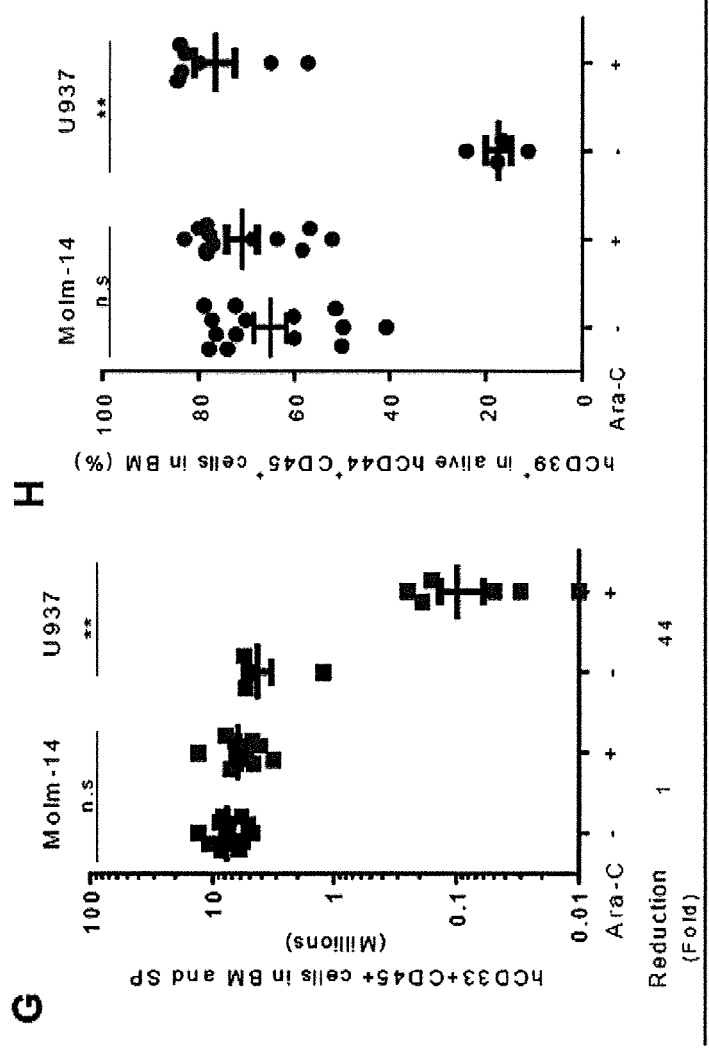

FIG. 2. Validation of the increase in CD39 after cytarabine (AraC) in 9 patient-derived xenografts, 45 AML patients and 2 cell line-derived xenografts. (A) The total number of human AML cells expressing CD45, CD33 and CD44 in 9 patient-derived xenograft (PDX) was analyzed and quantified using flow cytometry in AraC-treated xenografted mice compared to PBS-treated xenografted mice in bone marrow and spleen. (B) Flow cytometric analysis of the percent of $CD34^+CD38^-$ immature cell population was performed in human viable residual $CD45^+CD33^+$ AML cells from AraC-treated xenografted mice compared to PBS-treated xenografted mice in bone marrow. (C) The percent of $CD39^+$ cells in the bulk population and $CD34^+CD38^-$ immature cell population of human viable residual $CD45^+CD33^+$ AML cells was assessed in AraC-treated xenografted mice compared to PBS-treated xenografted mice in bone marrow by flow cytometry. (D-E-F) Similarly, flow cytometric analyses of 45 AML patients in peripheral blood at D35 (post-chemotherapy) and diagnosis to assess the percentage of blasts (D), of $CD34^+CD38^-$ immature cells (E), and of $CD39^+$ residual cells in both total blasts (bulk) and $CD34^+CD38^-$ population (F). (G-H) Flow cytometry analysis of 1 resistant cell line (MOLM14) and 1 sensitive cell line (U937)-derived xenograft (CLDX) to assess the total cell tumor burden of human viable AML cells in AraC- and PBS-treated CLDX (G), the percent of $CD39^+$ cells (H).

FIG. 3. In vitro study of the CD39 protein expression in MOLM14 AML cells after cytarabine (AraC) treatment in normoxia (21%) and hypoxia (1%). (A) Western analysis of the expression of HIF-1alpha, VDAC, CD39, P2Y13, pATF2 and HSP90 (as loading control) in MOLM14 cells after normoxia (21% $O_2$) or hypoxia (1% $O_2$) for 24 h, 48 h or 72 h. Each lane contained 30 μg of protein. (B-C-D) MOLM14 cells were treated with AraC (2 μM, IC50 in normoxia) for 48 h either in normoxia (21% $O_2$) or hypoxia (1% $O_2$). Flow cytometric analyses were perform to assess cell viability (B), $CD39^+$ expression (C-D). The results are representative of at least three independent experiments. The ATPase activity of CD39 in MOLM14 cells after Ara-C treatment was assessed and the concentration of non-hydrolyzed extracellular ATP was determined using the ATPlite assay (PerkinElmer) (E).

FIG. 4. In vitro potentiatingeffect of ARL67156 (CD39 inhibitor) with cytarabine (AraC) in MOLM14 cell line. (A-B) MOLM14 cells were either treated or not with 2 μM Ara-C, 100 μmol/L ARL or 250 μmol/L of another CD39 inhibitor, POM-1, for 48 h. Cell viability was assessed using AnnexinV/7AAD-based flow cytometry assay. (C) U937 AML cell line was either treated or not with 0.5 μM Ara-C or 100 μmol/L ARL. The percent of viable cells was analyzed using AnnexinV/7AAD-based flow cytometry assay.

EXAMPLE

Chemotherapy resistance is the major therapeutic barrier in acute myeloid leukemia (AML). AML is the most common adult leukemia. It is characterized by clonal expansion of immature myeloblasts and initiates from rare leukemic stem cells (LSCs). Despite a high rate of complete remission after conventional front-line induction chemotherapy (eg. daunorubicin, DNR, or idarubicin, IDA plus cytarabine, AraC), the prognosis is very poor in AML. To date, 5-year overall survival is still about 30 to 40% in patients younger than 60 years old and less than 20% in patients over 60 years. This results from the high frequency of distant relapses (50 and 85% before and after the age of 60, respectively) caused by tumor regrowth initiated by chemoresistant leukemic clones (RLCs) and characterized by a refractory phase during which no other treatment has shown any efficacy thus far (Tallman et al. 2005; Burnett et al. 2011). AML is one of the rare hematological malignancies, for which therapy has not significantly improved during the past 30 years despite intense research efforts. Therefore, understanding the causes of chemoresistance is crucial for the development of new treatments eradicating RLCs to overcome AML patient relapses.

The biology of therapeutic resistance (drug efflux, detoxification enzymes, inaccessibility of the drug to the leukemic niche) currently represents an active area of research. However, the molecular mechanisms underlying AML chemoresistance are still poorly understood, especially in vivo. It is nevertheless increasingly recognized that the causes of chemoresistance and relapse reside within a small cell population. Supporting this idea, a recent clinical study by our Team has shown that the presence of high levels of CD34$^+$CD38$^{low/-}$CD123$^+$cells at diagnosis correlates with adverse outcome in AML patients in terms of response to therapy and overall survival (Vergez et al. 2011). Consistent with these data, Ishikawa and colleagues (2007) have observed that this population is also the most resistant to AraC in vivo. As a first step towards successful therapeutic eradication of these RLCs, it is now necessary to comprehensively profile their dominant intrinsic and acquired characteristics.

Until recently, mouse models of AML have been extensively used to characterize the nature and origin of LSCs (in part by our group: Sanchez et al. 2009. Sarry et al. 2011), but less frequently used to study their chemoresistance and miminum residual disease in vivo, an approach that is crucial to improve therapeutic outcome of AML patients. Thus, we tested and established an appropriate dose and regimen for use of AraC as baseline cytotoxic in our NSG mice xenografted with primary AML cells from patients seen at diagnosis or relapse of disease. We have access to a large resource of primary samples through our Biobank of the Hematology Clinical Department of the Oncopole Hospital in Toulouse (HIMIP, INSERM-U1037, ~150 patients newly diagnosed/year) and in collaboration with Drs Gwen Danet-Desnoyers and Martin Carroll (University of Pennsylvania, Pa., USA). Then, we analyzed human AML cells surviving after AraC treatment over time. Most noteworthy, we have shown a significant cytoreduction of the peripheral engraftment and total cell tumor burden in all patients tested with AraC and a variable duration (2-7 weeks) of response from patient-to-patient as we see in clinics, demonstrating that we have established a powerful preclinical model to screen in vivo responses to conventional genotoxics and to mimic the chemoresistance and minimal residual disease as observed in AML patients after chemotherapy (Farge T, Sarry J E et al, Chemotherapy resistant human acute myeloid leukemia cells are not enriched for leukemic stem cells but require oxidative metabolism. CANCER DISCOVERY. 2017).

Based on this model and the current hypothesis that AraC-resistant cells are rare, replicatively dormant and well adapted to hypoxic conditions (Ishikawa et al. 2007; Raaijmakers, 2011; Wilson and Hay, 2011), we have further analyzed all of these characteristics in AraC-treated patient-xenografted mice. We have first confirmed that CD34$^+$CD38$^-$ cell population is increased post-AraC chemotherapy in residual AML cells. Surprisingly, we have found that AraC treatment equally kills both cycling and quiescent cells as well as LSCs in vivo. Moreover, we observed that AraC chemotherapy induced a ROS-/MMP-dependent apoptotic cell death in vivo and AraC-resistant AML cells exhibit metabolic features and gene signatures consistent with a HIGH oxidative phosphorylation (OXPHOS) status. Finally, we have identified a signature of 15 genes (amongst of 350 genes, including CD39/ENTPD1 and P2Y13), that are the most differentially expressed in all of the three AML patient-derived xenografts after AraC treatment as compared to control samples using our in vivo PDX models coupled to a gene expression analysis (FIG. 1a).

CD39 is a new player and target of AraC resistance mechanism in acute myeloid leukemia in vivo. CD39/ENTPD1 (ectonucleoside triphosphate diphosphohydrolase-1) is a protein of the membrane surface, actor of the adenosine signaling pathway. In fact, CD39 decreases extracellular ATP (immunogenic inducer) and generates immunosuppressive adenosine, which potently inhibits host immune responses against cancer. CD39 also has a role in the immunosurveillance and inflammatory response. Furthermore, although other NTPDases exist, CD39 appears to be the main NTPDase in T lymphocytes and regulatory T cells (CD4+CD25+Foxp3+) (Bastid et al. 2013).

Recent lines of evidence have revealed high expression and activity of CD39 in several blood or solid tumors (head and neck cancer, thyroid cancer, colon cancer, pancreatic cancer, kidney cancer, testis cancer, and ovarian cancer), implicating potential roles for this enzyme in promoting tumor growth and infiltration (Bastid et al. 2015). Also, CD39 is frequently detected in primary tumor cells, cancer exosomes, tumor associated endothelial cells and AML blasts. CD39 contributes to the immunosuppressive microenvironment in AML (Dulphy et al. 2014). In fact, extracellular nucleotides (ATP, UTP) can inhibit AML homing and engraftment in NSG mice (Salvestrini et al. 2012). In other hand, the second target P2Y13 belongs to the G-Protein-coupled receptor family (a purinergic ADP-receptor) that decreases extracellular ADP. P2Y13 is overexpressed in human monocytes, T cells, and dendritic cells derived from blood monocytes or bone marrow, which suggest that it might play a role in hematopoiesis and the immune system. P2Y13 has a role in up-regulation of HDL-c metabolism (Goffinet et al. 2014) and also plays an important role in the balance of osteoblast and adipocyte terminal differentiation of bone marrow progenitors (Biver et al. 2013).

Figure 1B:
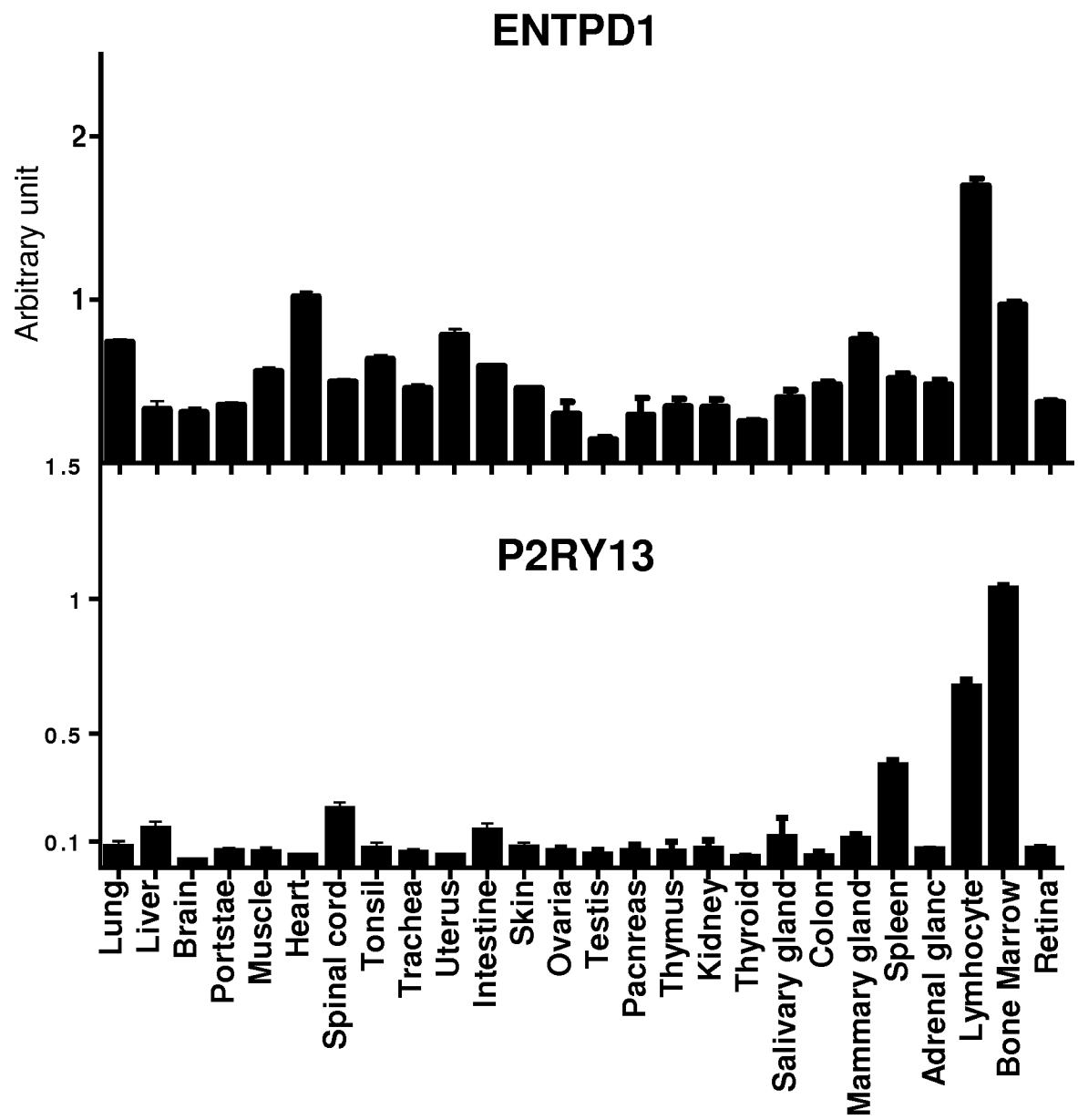
Figure 1C:
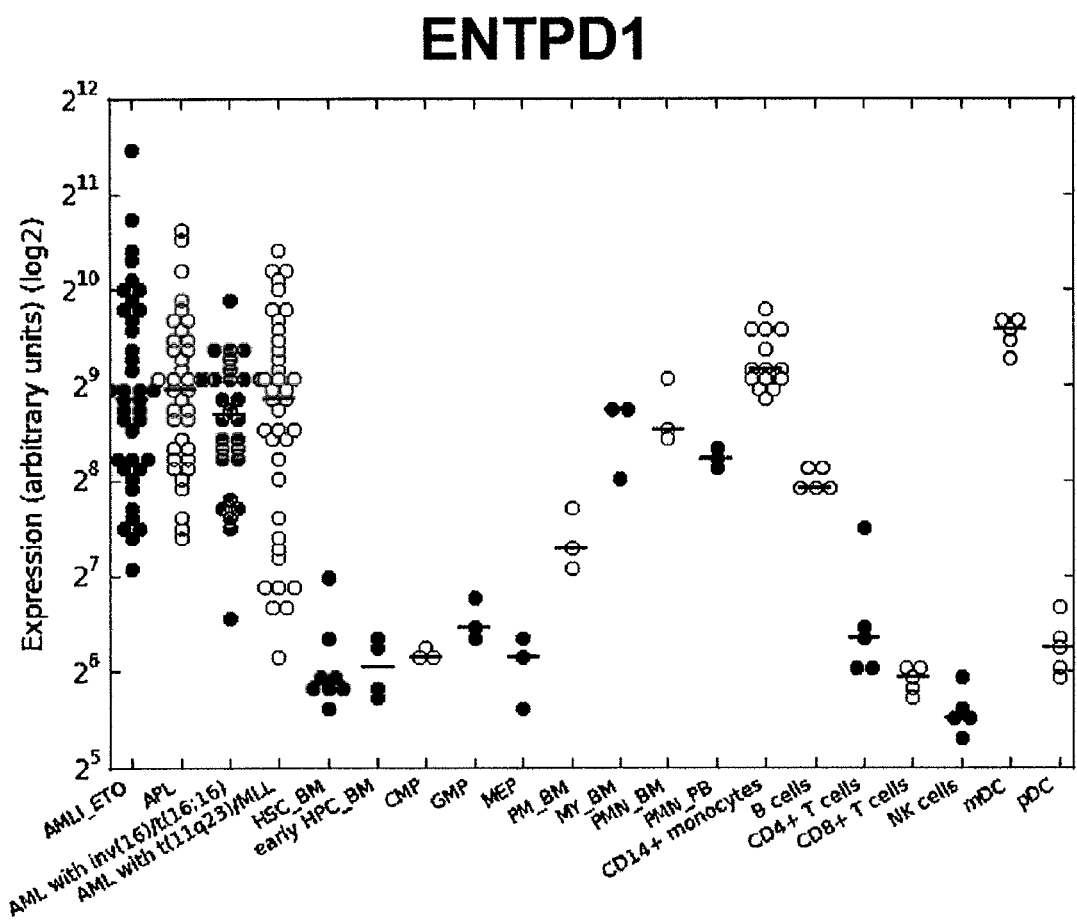
Figure 1C:
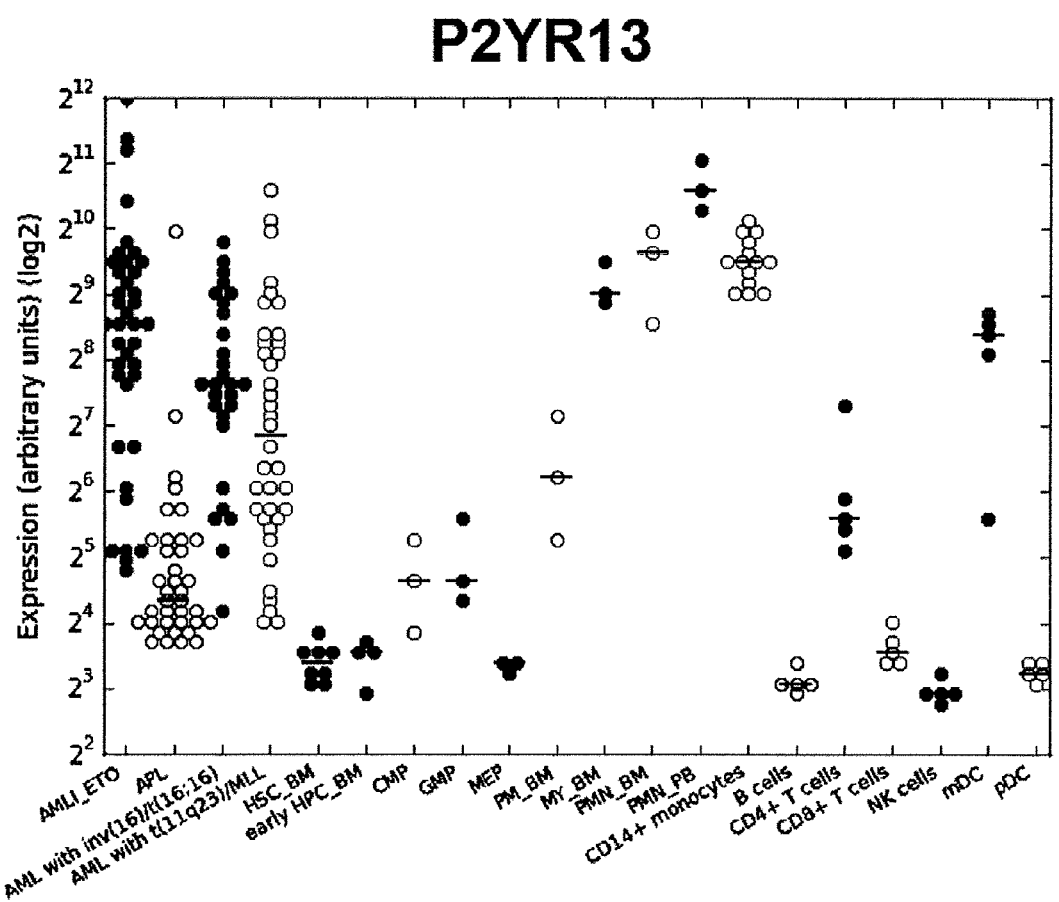
Figure 1D:
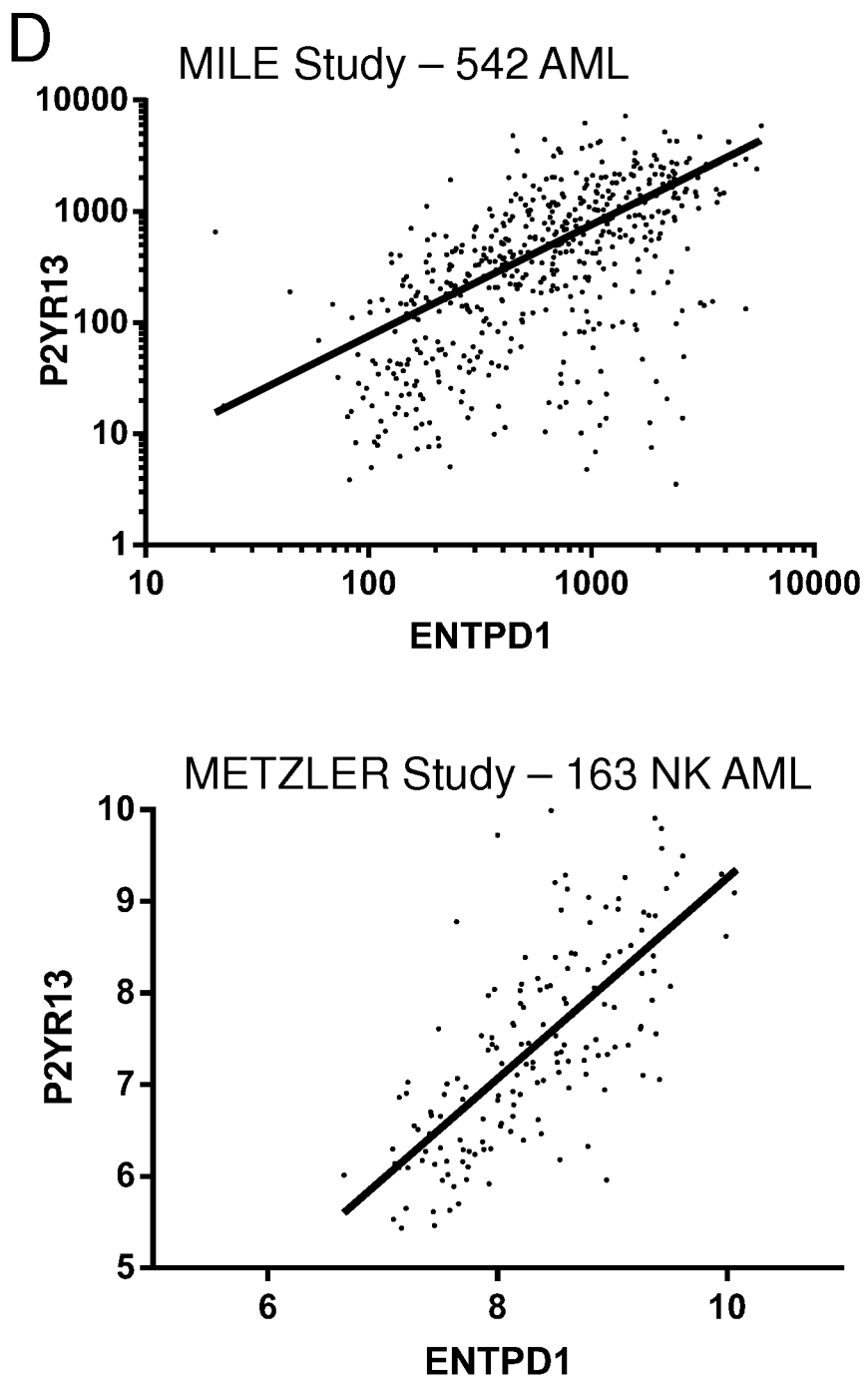

As it can be seen in FIG. 1b, the expression analysis of CD39/ENTPD1 and P2Y13 through various tissues in human shows a similar tissue distribution profiling and a concordant overexpression in bone marrow and lymphocytes. Furthermore, CD39 and P2Y13 are co-expressed in hematopoietic cells as analyzed in the Hemaexplorer public database (FIG. 1c). In this regard, they are strikingly upregulated in normal monocytes and AML patient cells (FIG. 1c). Finally, we have shown co-expression between CD39 and P2Y13 in AML patient cells from two independent patient cohorts with gene expression data (MILE and METZLER studies; FIG. 1d). This suggests that AML patients might be stratified in two groups "high and low" based on their CD39/P2Y13 gene expression. Taking together our preliminary data and those observations from the literature, we aimed to focus on the expression levels of CD39 in response to cytarabine treatment and to explore the signaling axis involving CD39-P2Y13 in the chemoresistance of AML.

Validation of the increase in CD39 expression in 9 patient-derived xenograft (PDX) models treated with cytarabine and in 45 AML patients at D35 compared to diagnosis. We first examined the effect of AraC on CD39 expression in residual viable AML cells from our NSG model xenografted with primary AML cells from 9 patients (FIG. 2a). Consistent to what we have already shown, we have a significant cytoreduction of the total cell tumor burden in bone marrow and spleen in vivo associated with an increase in the CD34$^+$CD38$^-$ population post-AraC treatment in our PDX model (FIG. 2a). Furthermore, there is an increase in percent of CD39 cells not only in bulk but also in the immature CD34$^+$CD38$^-$ population from AraC-treated mice compared to control mice (FIG. 2a). In accordance with our preclinical model, the analysis of 45 AML patients at the diagnosis (DX) and after significant tumor reduction or complete remission (D35) also showed an increase in CD34$^+$CD38$^-$population and in CD39 cells in the residual bulk and immature populations at day 35 post-AraC treatment (FIG. 2b). Then, we analyzed CD39 expression in two AML cell line-derived xenografts, which confirmed our previous results in patients and PDXs. In fact, the CD39 expression increases in the sensitive cell line (U937) post-AraC treatment compared to vehicle-treated CLDX model, consistently with a significant cytoreduction of the total cell tumor burden in bone marrow and spleen (FIG. 2g-h). In the other hand, any significant tumor reduction was observed in the resistant cell line (MOLM14)-derived xenograft, associated with a High CD39 expression in vehicle mice, which seems to be comparable to the CD39 expression level in the sensitive cell line (U937) post-AraC treatment.

Figure 3A:
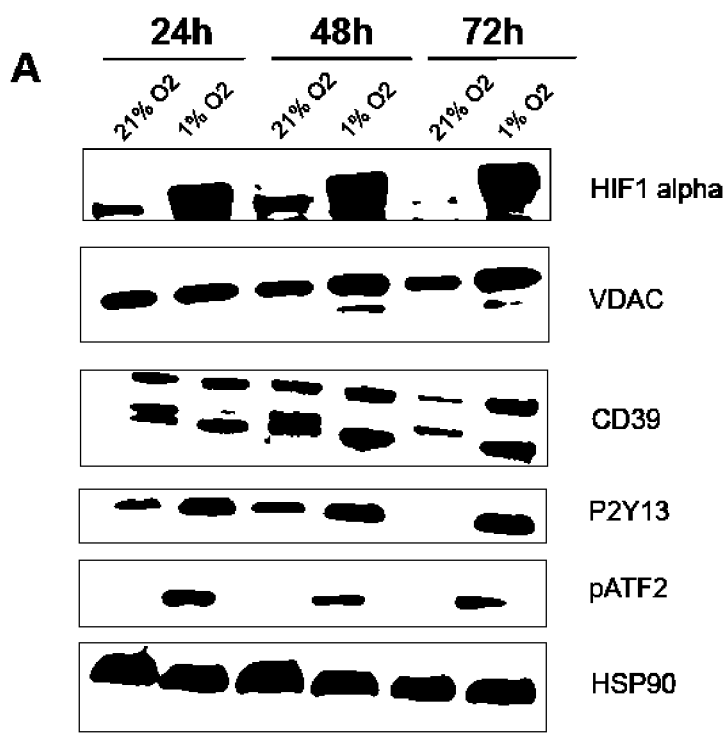
Figure 3B:
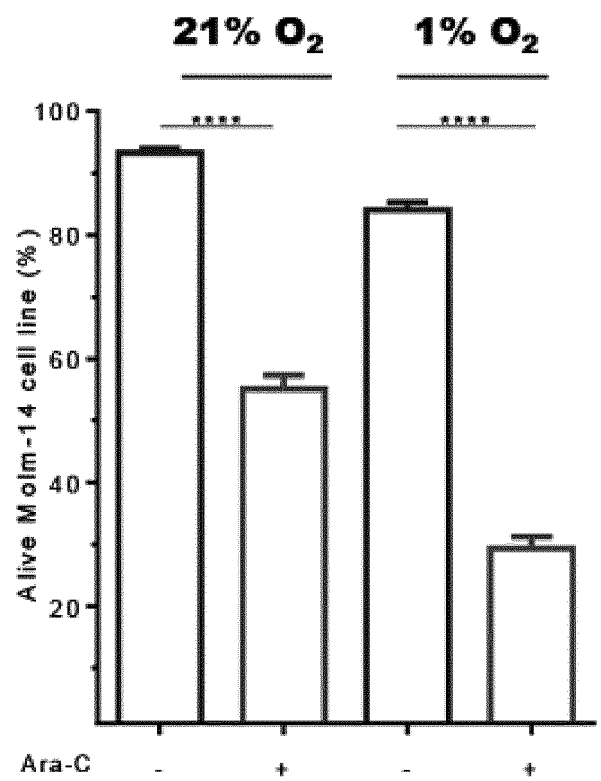
Figures 3C, 3D:
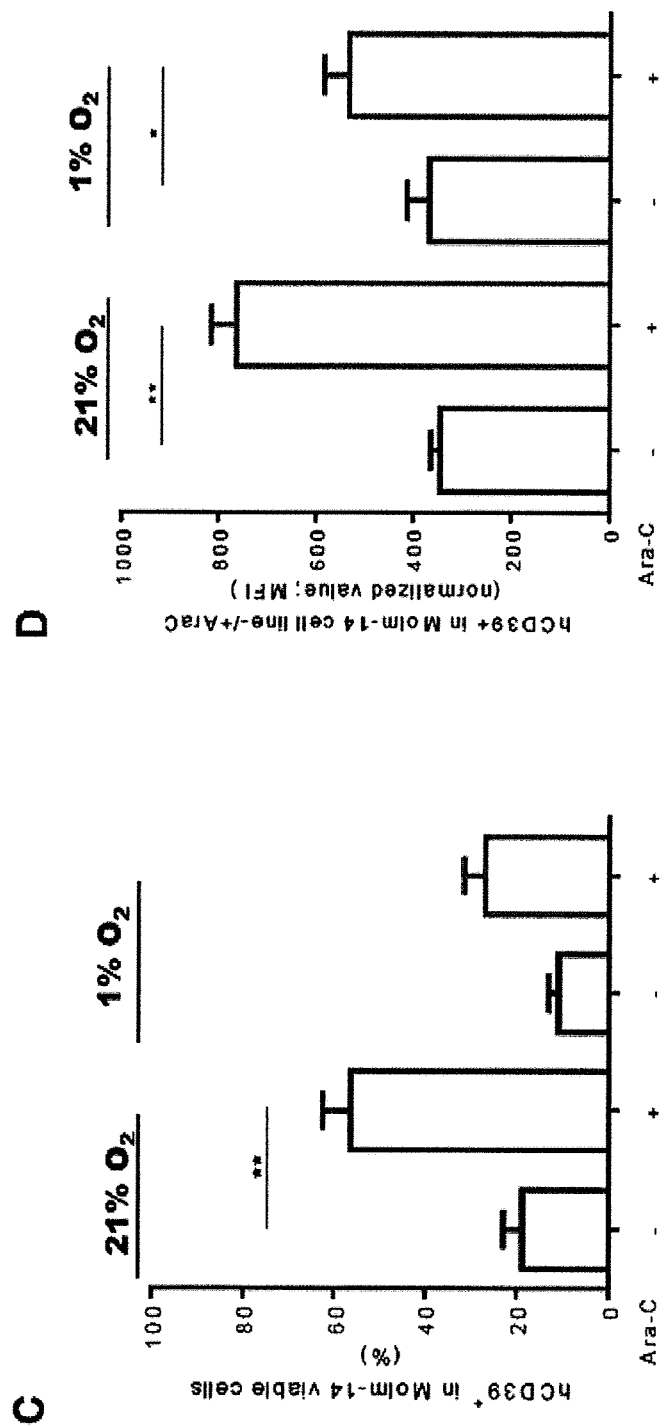
Figure 3E:
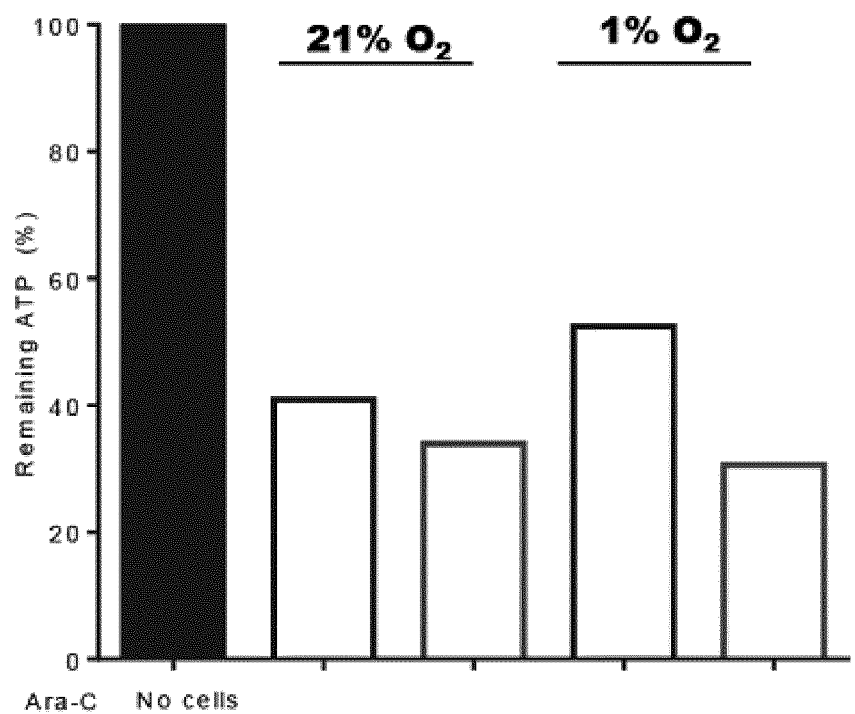

In vitro increase of the CD39 expression in AML MOLM-14 cell line after cytarabine treatment in normoxia and hypoxia. Then, we have established an AML cell line model to further study this mechanism. Using MOLM14 AML cell lines and hypoxic condition (1% versus 21% $O_2$), we have analyzed the CD39 expression and ATP-hydrolyzing activity (FIG. 3). We first observed the induction of hypoxic markers such as HIF1a and VDAC, as well as CD39 in a time-dependent manner (FIG. 3a), which might suggest a link of CD39 with mitochondrial function under hypoxia. Next, we confirmed that AraC treatment increased the percent and expression of CD39 in residual viable MOLM14 cells in both normoxic and hypoxic conditions (FIG. 3b-d). Similar to the increase of CD39 expression in MOLM14 cells, we observed a significant decrease of the remaining ATP after AraC in both normoxic and hypoxic conditions, suggesting a proportional increase of the ATP-hydrolyzing activity of CD39 in AraC-residual MOLM14 cells (FIG. 3e). Note of attention, hypoxia did not increase surface CD39 expression and activity (FIG. 3c-e) in basal condition (eg. in absence of AraC) while increase the expression of total CD39 protein (Western blot, FIG. 3a).

Figures 4A, 4B:
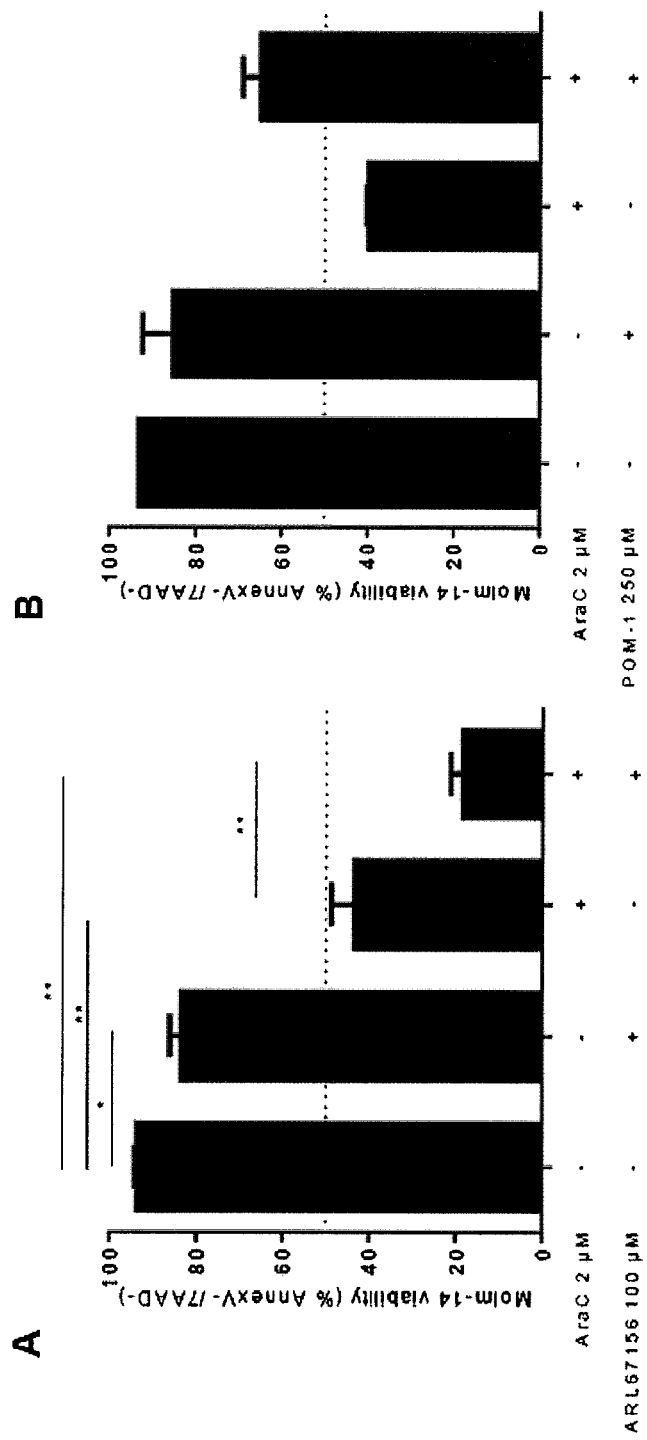
Figure 4C:
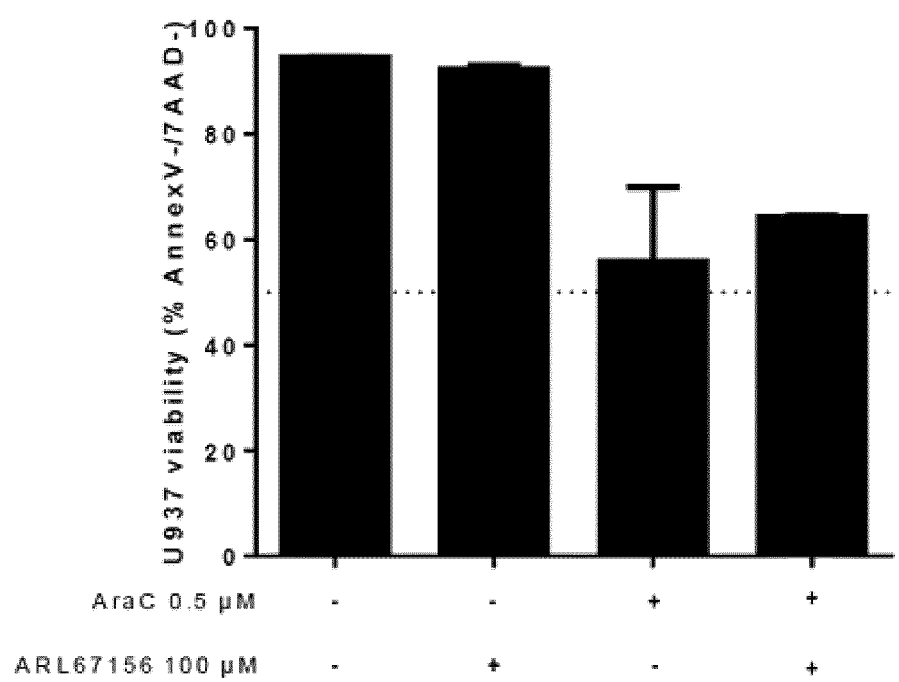

In vitro potentiating effect of CD39 inhibitor with cytarabine in MOLM14 cell line. In order to explore the effect of CD39 onto the chemoresistance to AraC in AML cell lines in vitro, we first tested the consequence of CD39 inhibition using an ecto-ATPase inhibitor ARL67156. While ARL67156 inhibitor did not induce cell death alone (eg. in absence of AraC), we observed a potentiatingeffect of ARL67156 with AraC in Molm-14 cell line (FIG. 4a). In the other hand, another CD39 inhibitor, POM-1, did not induce a potentiating effect in combination with AraC treatment but seems to have a protective effect, suggesting the activation of a compensatory mechanism (FIG. 4b) Also, the treatment of U937 cell line with ARL67156 inhibitor did not potentiate the effect of AraC in inducing cell death (FIG. 4c). High ADP and/or P2YR13 activation might be involved into this compensatory and protective mechanism.

REFERENCES

Throughout this application, various references describe the state of the art to which this invention pertains. The disclosures of these references are hereby incorporated by reference into the present disclosure.

The invention claimed is:
1. A method of treating chemoresistant acute myeloid leukemia (AML) in a patient in need thereof, wherein residual chemoresistant AML cells of the patient exhibit increased expression of CD39 compared to primary AML cells, comprising, administering to the patient a therapeutically effective amount of cytarabine and an inhibitor of the CD39-P2Y13-cAMP-PKA signaling axis,
   wherein the therapeutically effective amount is sufficient to decrease the generation of adenosine by CD39 and prevent immunosuppression,
   wherein the inhibitor of the CD39-P2Y13-cAMP-PKA signaling axis is not suramin; and
   wherein the inhibitor of the CD39-P2Y13-cAMP-PKA signaling axis is a CD39 inhibitor, an antibody having specificity for CD39, or an inhibitor of CD39 expression.
2. The method of claim 1 wherein the leukemia is resistant to a combination of daunorubicin, or idarubicin plus cytarabine (AraC).

* * * * *